US012208221B2

(12) United States Patent
Kallmes et al.

(10) Patent No.: US 12,208,221 B2
(45) Date of Patent: Jan. 28, 2025

(54) BALLOON GUIDING SHEATH HAVING A TEXTURED SURFACE

(71) Applicants: Marblehead Medical, LLC, Rochester, MN (US); Mayo Foundation for Medical Education and Research, Rochester, MN (US)

(72) Inventors: David F. Kallmes, Rochester, MN (US); Waleed Brinjikji, Rochester, MN (US); Brady Hatcher, Rogers, MN (US); Randy Beyreis, Rogers, MN (US)

(73) Assignees: Covidien LP, Mansfield, MA (US); Mayo Foundation for Medical Education and Research, Rochester, MN (US)

( * ) Notice: Subject to any disclaimer, the term of this patent is extended or adjusted under 35 U.S.C. 154(b) by 309 days.

(21) Appl. No.: 17/222,798

(22) Filed: Apr. 5, 2021

(65) Prior Publication Data
US 2021/0316116 A1 Oct. 14, 2021

Related U.S. Application Data

(60) Provisional application No. 63/036,364, filed on Jun. 8, 2020, provisional application No. 63/006,830, filed on Apr. 8, 2020.

(51) Int. Cl.
*A61M 25/10* (2013.01)
*A61M 25/00* (2006.01)
*A61M 25/01* (2006.01)

(52) U.S. Cl.
CPC .... *A61M 25/0155* (2013.01); *A61M 25/0043* (2013.01); *A61M 25/0122* (2013.01);
(Continued)

(58) Field of Classification Search
CPC .......... A61M 25/0155; A61M 25/0043; A61M 2025/006; A61M 25/0122;
(Continued)

(56) References Cited

U.S. PATENT DOCUMENTS

| 5,728,065 A | 3/1998 | Follmer et al. |
| 6,514,228 B1 * | 2/2003 | Hamilton ................ A61F 2/958 |
| | | 604/102.03 |

(Continued)

FOREIGN PATENT DOCUMENTS

| WO | 9830269 | 7/1998 |
| WO | 2015073114 A1 | 5/2015 |
| WO | 2020018653 A1 | 1/2020 |

OTHER PUBLICATIONS

First Office Action and Search Report, and translation thereof, from counterpart Chinese Application No. 202110387152.1 dated Nov. 2, 2022, 15 pp.
(Continued)

Primary Examiner — Nathan R Price
Assistant Examiner — Anna E Goldberg-Richmeier
(74) Attorney, Agent, or Firm — Shumaker & Sieffert, P.A.

(57) ABSTRACT

A balloon guiding sheath may include an elongated sheath comprising a proximal end, a distal end, an inner tube, an outer tube surrounding the inner tube, an access port located adjacent the proximal end, a distal port located adjacent the distal end, and a working lumen extending between the access port and the distal port. The balloon guiding sheath may also include an inflatable balloon located on an outer surface of the elongated sheath adjacent the distal end. The balloon guiding sheath may also include a textured surface located along an outer portion of the outer tube and located beneath the inflatable balloon. The elongated sheath may be sized and configured to enable direct insertion into vascu-
(Continued)

lature of a patient through an arteriotomy in at least one of a carotid artery or a vertebral artery to position the inflatable balloon at a target site.

18 Claims, 13 Drawing Sheets

(52) U.S. Cl.
CPC ... *A61M 25/0021* (2013.01); *A61M 2025/006* (2013.01); *A61M 2025/1088* (2013.01)

(58) Field of Classification Search
CPC ...... A61M 2025/1088; A61M 25/0021; A61M 25/1018; A61M 25/10184
See application file for complete search history.

(56) References Cited

U.S. PATENT DOCUMENTS

| | | | |
|---|---|---|---|
| 6,638,245 B2 | 10/2003 | Miller et al. | |
| 6,702,782 B2 | 3/2004 | Miller et al. | |
| 7,537,580 B2 | 5/2009 | Willard | |
| 7,780,626 B2 * | 8/2010 | Wu | A61M 25/0014 604/523 |
| 9,504,809 B2 * | 11/2016 | Bo | A61M 27/00 |
| 9,655,755 B2 | 5/2017 | Chou et al. | |
| 2003/0199914 A1 * | 10/2003 | Diaz | A61M 25/104 606/194 |
| 2013/0281788 A1 * | 10/2013 | Garrison | A61B 17/221 606/127 |
| 2014/0107575 A1 | 4/2014 | Miller et al. | |
| 2015/0367107 A1 * | 12/2015 | Rivera | A61M 25/1036 606/192 |
| 2019/0110826 A1 | 4/2019 | Goshayeshgar et al. | |
| 2019/0381287 A1 | 12/2019 | Mock et al. | |
| 2021/0138205 A1 * | 5/2021 | Guyon | A61M 25/10 |

OTHER PUBLICATIONS

Extended Search Report from counterpart European Application No. 21167141.7, dated Oct. 15, 2021, 9 pp.
Response to Communication Pursuant to Rules 70(2) and 70a(2) EPC dated Nov. 22, 2021, from counterpart European Application No. 21167141.7, filed May 16, 2022, 17 pp.
Response to Examination Report dated Feb. 29, 2024, from counterpart European Application No. 21167141.7 filed Jun. 27, 2024, 48 pp.
Communication pursuant to Article 94(3) EPC from counterpart European Application No. 21167141.7 dated Feb. 29, 2024, 4 pp.

* cited by examiner

BALLOON GUIDING SHEATH HAVING A TEXTURED SURFACE

This application claims the benefit of U.S. Provisional Application No. 63/006,830, filed Apr. 8, 2020, and entitled, "BALLOON GUIDING SHEATH HAVING A TEXTURED SURFACE," and U.S. Provisional Application No. 63/036,364, filed Jun. 8, 2020, and entitled, "BALLOON GUIDING SHEATH HAVING A TEXTURED SURFACE," each of which is incorporated herein by reference in its entirety.

GOVERNMENT SPONSORED RESEARCH OR DEVELOPMENT

This invention was made with government support under Grant Numbers 1R41NS103670-01A1 and 2R44NS103670-02 awarded by the National Institute of Neurological Disorders and Stroke (NINDS), which is part of the National Institutes of Health (NIH). The Government has certain rights in the invention.

TECHNICAL FIELD

The invention relates generally to medical devices and methods of use. Embodiments of the invention include devices for performing thrombectomy or embolectomy in the internal carotid artery and other vessels of a patient.

BACKGROUND

Mechanical thrombectomy is a procedure that removes clots through endovascular intervention to restore blood flow to the brain during acute ischemic stroke. Acute Ischemic Stroke ("AIS") can be caused by thrombus, embolus or other occlusions in regions of the internal carotid artery ("ICA") such as the Petrous segment, Cavernous segment or Cerebral segment, or the middle cerebral artery ("MCA"), such as the MCA bifurcation, the M1 segment, and the M2 segment. Approaches for performing thrombectomy or embolectomy to treat AIS include accessing the vasculature and navigating a balloon guiding catheter to the carotid artery at a location upstream from the occlusion, typically at a proximal location in the artery such as the cervical segment of the ICA. After the balloon is inflated to provide antegrade blood flow cessation, retrieval devices can be passed through the balloon guide catheter to retrieve the embolus. Thrombectomy tools such as stent retrievers, aspiration catheters, or both can be delivered directly to the embolus through the guiding catheter to complete the retrieval process, after which the balloon is deflated and the retrieval and guide catheters retracted to the access point.

These thrombectomy procedures may involve placing a sheath through an arteriotomy in the patient's common femoral artery, and delivering the guiding catheter to the ICA through the sheath. In some cases, the arteriotomy may be located in an artery other than the common femoral artery. For example, an 8-9 French (Fr) inner diameter (ID) (0.015-0.118 inches) sheath having a length on the order of twenty-five centimeters can be used to provide the access to the arterial tree through the arteriotomy. A balloon guiding catheter having a 7-8 Fr outer diameter (OD) (0.092-0.105 inches), commonly about ninety centimeters in length, can then be delivered to the ICA through the sheath. An arteriotomy of 0.131-0.144 inches may be required for the sheath during procedures of these types. Unfortunately, these relatively large arteriotomies can enhance the risk of bleeding, especially since patients undergoing these procedures may be receiving thrombolytics that may increase the risks of hemorrhagic complications.

Distal access aspiration catheters (e.g., up to about 0.087 inch OD) are sometimes used during thrombectomy in the ICA. Such distal aspiration catheters include the ACE 68 from Penumbra, Inc. and the Sophia Plus from Microvention, Inc. For example, during these procedures the distal aspiration catheter can be inserted with the end positioned at the distal middle cerebral artery. Other thrombectomy tools such as stent retrievers are sometimes delivered to the intracranial vasculature through distal access catheters used in this manner, or directly through the guide catheter. However, balloon guiding catheters have IDs that are too small to accommodate these distal aspiration catheters. Other known balloon guide catheters include the Cello devices from Medtronic, Inc., and the Flowgate2 device from Stryker Neurovascular. The relatively long period of time required to place a sheath and then a balloon guide catheter can detract from the benefits of this treatment.

Stent retrievers and other endovascular tools are sometimes placed in the ICA or other vasculature using guiding sheaths that do not have balloons. Guiding sheaths are typically about ninety centimeters in length. These devices act as a combination of access sheath and guiding catheter. The need for a separate sheath is obviated by the use of these guiding sheaths since they are sufficiently long to provide access to the target vessel. Although guiding sheaths do not provide arterial occlusion, they can be rapidly placed.

SUMMARY

The disclosure includes a balloon guiding sheath, comprising an elongated sheath having a proximal end, a distal end, an inner tube extending between the proximal end and the distal end, an outer tube surrounding the inner tube and extending between the proximal end and the distal end, an access port located adjacent the proximal end, a distal port located adjacent the distal end, and a working lumen extending through an interior portion of the elongated sheath between the access port and the distal port; an inflatable balloon located on an outer surface of the elongated sheath adjacent the distal end, the inflatable balloon being fluidly coupled to an inflation lumen extending between the inflatable balloon and an inflation port located adjacent the proximal end; and a textured surface located along an outer portion of the outer tube and located beneath the inflatable balloon. In some embodiments, the elongated sheath is sized and configured to enable direct insertion into a patient's vasculature through an arteriotomy in at least one of a carotid artery or a vertebral artery to position the inflatable balloon at a target site.

In some embodiments, the textured surface is located between the inflatable balloon and the inner tube. The textured surface may define at least one raised surface and at least one lowered surface. In some embodiments, the textured surface rotationally extends around at least a portion of a perimeter of the outer tube. The textured surface may rotationally extend 360-degrees around the perimeter of the outer tube.

In some embodiments, the textured surface defines a first area, and an inflatable portion of the inflatable balloon defines a second area, and wherein the second area is greater than the first area. The textured surface may be entirely located beneath the inflatable balloon. In some embodiments, the textured surface comprises a cross-hatched surface. The textured surface may define a cross-sectional profile defining a rectangular shape. In some embodiments, the textured surface defines a cross-sectional profile defining a triangular shape. The textured surface may be arranged and configured to reduce a contact area between the outer tube and the inflatable balloon when the inflatable balloon is deflated. In some embodiments, the textured surface is arranged and configured to reduce surface energy between the outer tube and the inflatable balloon. The textured surface may be located adjacent the distal end of the elongated sheath. In some embodiments, the textured surface is located closer to a proximal portion of the inflatable balloon than a distal portion of the inflatable balloon. The elongated sheath may define a generally constant outer diameter from the proximal end to the distal end.

The disclosure also includes a method of using a balloon guiding sheath comprising an elongated sheath having a proximal end, a distal end, an inner tube extending between the proximal end and the distal end, an outer tube surrounding the inner tube and extending between the proximal end and the distal end, an access port located adjacent the proximal end, a distal port located adjacent the distal end, a working lumen extending through an interior portion of the elongated sheath between the access port and the distal port, and an inflatable balloon located on an outer surface of the elongated sheath adjacent the distal end, the inflatable balloon being fluidly coupled to an inflation lumen extending between the inflatable balloon and an inflation port located adjacent the proximal end. In some embodiments, the method comprises inserting the balloon guiding sheath directly into a patient's vasculature through an arteriotomy in at least one of a carotid artery or a vertebral artery; advancing the balloon guiding sheath through the patient's vasculature and positioning the distal end at a target site; and providing a textured surface located along an outer portion of the outer tube beneath the inflatable balloon and thereby inflating the inflatable balloon.

In some embodiments, the method includes substantially symmetrically inflating the inflatable balloon. The method may include substantially symmetrically separating the inflatable balloon from the textured surface. In some embodiments, the method includes reducing surface contact between the inflatable balloon and the outer tube via the textured surface. The method may include, in response to reducing the surface contact between the inflatable balloon and the outer tube (when the balloon is deflated), substantially symmetrically inflating the inflatable balloon. In some embodiments, the method includes, in response to reducing the surface contact between the inflatable balloon and the outer tube (when the balloon is deflated), substantially symmetrically separating the inflatable balloon from the textured surface.

The method may further include reducing surface energy between the inflatable balloon and the outer tube via the textured surface. In some embodiments, the method includes, in response to reducing the surface energy between the inflatable balloon and the outer tube, substantially symmetrically inflating the inflatable balloon. The method may include, in response to reducing the surface energy between the inflatable balloon and the outer tube, substantially symmetrically separating the inflatable balloon from the textured surface. In some embodiments, the method includes flowing at least one of fluid or media over the textured surface.

BRIEF DESCRIPTION OF THE DRAWINGS

These and other features, aspects, and advantages are described below with reference to the drawings, which are intended to illustrate, but not to limit, the invention. In the drawings, like reference characters denote corresponding features consistently throughout similar embodiments.

DETAILED DESCRIPTION

Figure 1:
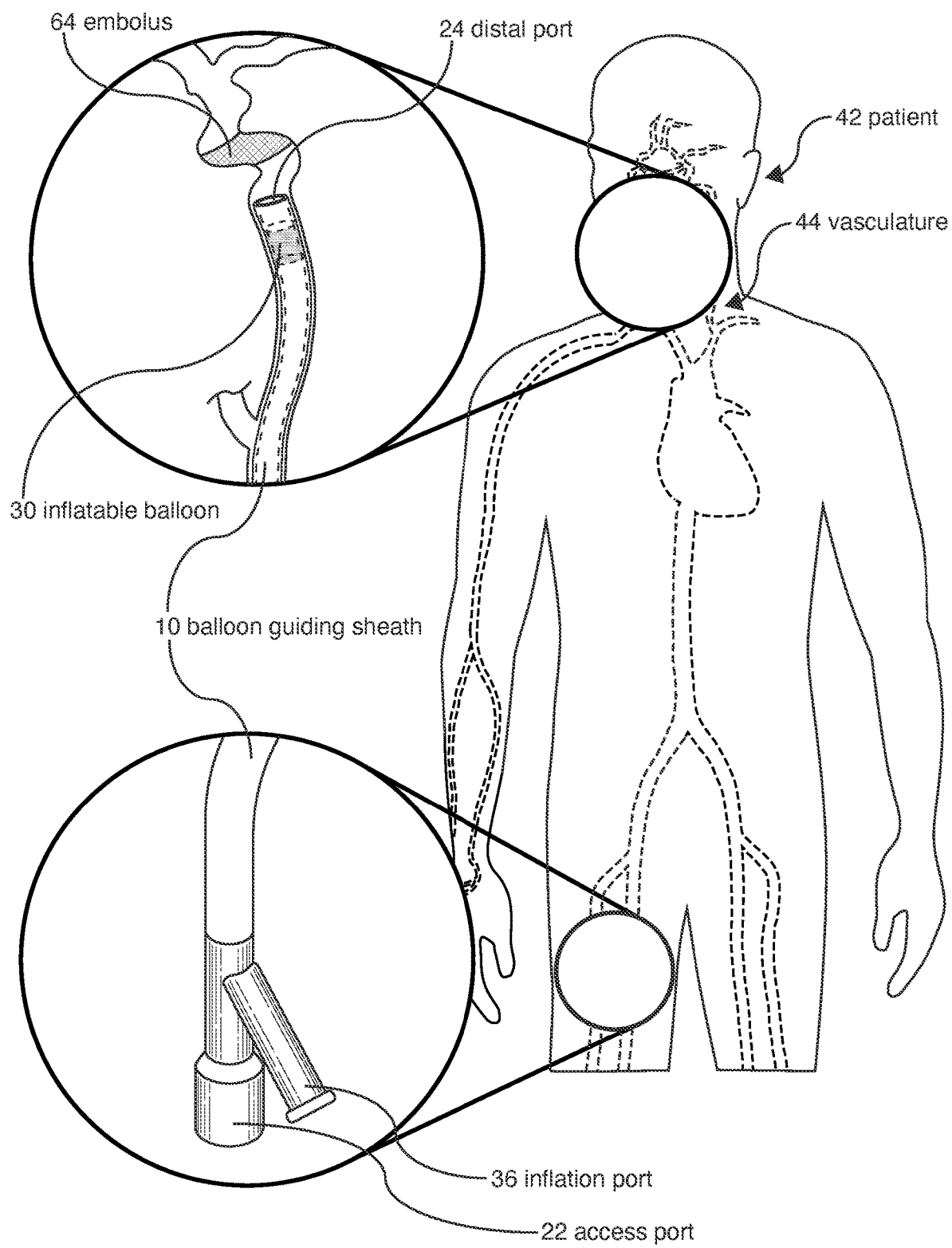
FIG. 1 illustrates a diagrammatic view of a balloon guiding sheath in a patient, according to some embodiments.

Although certain embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative ony and not intended to be limiting.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

COMPONENT INDEX

10—balloon guiding sheath
12—elongated sheath
14—proximal end (of elongated sheath)

16—distal end (of elongated sheath)
18—inner tube
20—outer tube
22—access port
24—distal port
26—working lumen
28—interior portion
30—inflatable balloon
32—outer surface (of elongated sheath)
34—inflation lumen
36—inflation port
38—textured surface
42—patient
44—vasculature
44a—common carotid artery
44b—internal carotid artery
44c—external carotid artery
44d—middle cerebral artery
44e—anterior cerebral artery
46—arteriotomy
48—target site
52—perimeter (of outer tube)
60—proximal portion (of inflatable balloon)
62—distal portion (of inflatable balloon)
64—embolus
66—inflation holes
68—inflation trough There is a continuing need for improved devices and methods for performing mechanical revascularization such as thrombectomy and embolectomy in the ICA and other vasculature. In particular, there is a need for such devices and methods that provide effective navigation to the target artery, support while advancing retrieval devices, and rapid flow arrest. Devices and methods of these types that can improve the efficiency of health care delivery would be especially desirable.

FIG. 1 illustrates a diagrammatic view of a patient 42 undergoing a embolectomy (or thrombectomy) procedure using a balloon guiding sheath 10, which, in many embodiments, is a balloon guide catheter capable of direct arterial access without an introducer sheath. As shown in FIG. 1, in some embodiments, the balloon guiding sheath 10 is sized and configured to be inserted in an arteriotomy located on the thigh of the patient 42 in order to reach a target site via femoral access. The arteriotomy may be located in another area of the patient's 42 vasculature 44, such as near the groin of the patient 42 in order to reach the target site via the patient's 42 femoral artery. In some embodiments, the arteriotomy is located near the wrist of the patient 42 to reach the target site via transradial arterial access. The arteriotomy may also be located in the patient's 42 vertebral artery. In many embodiments, the target site is located in a carotid artery of the patient 42.

Figure 2:
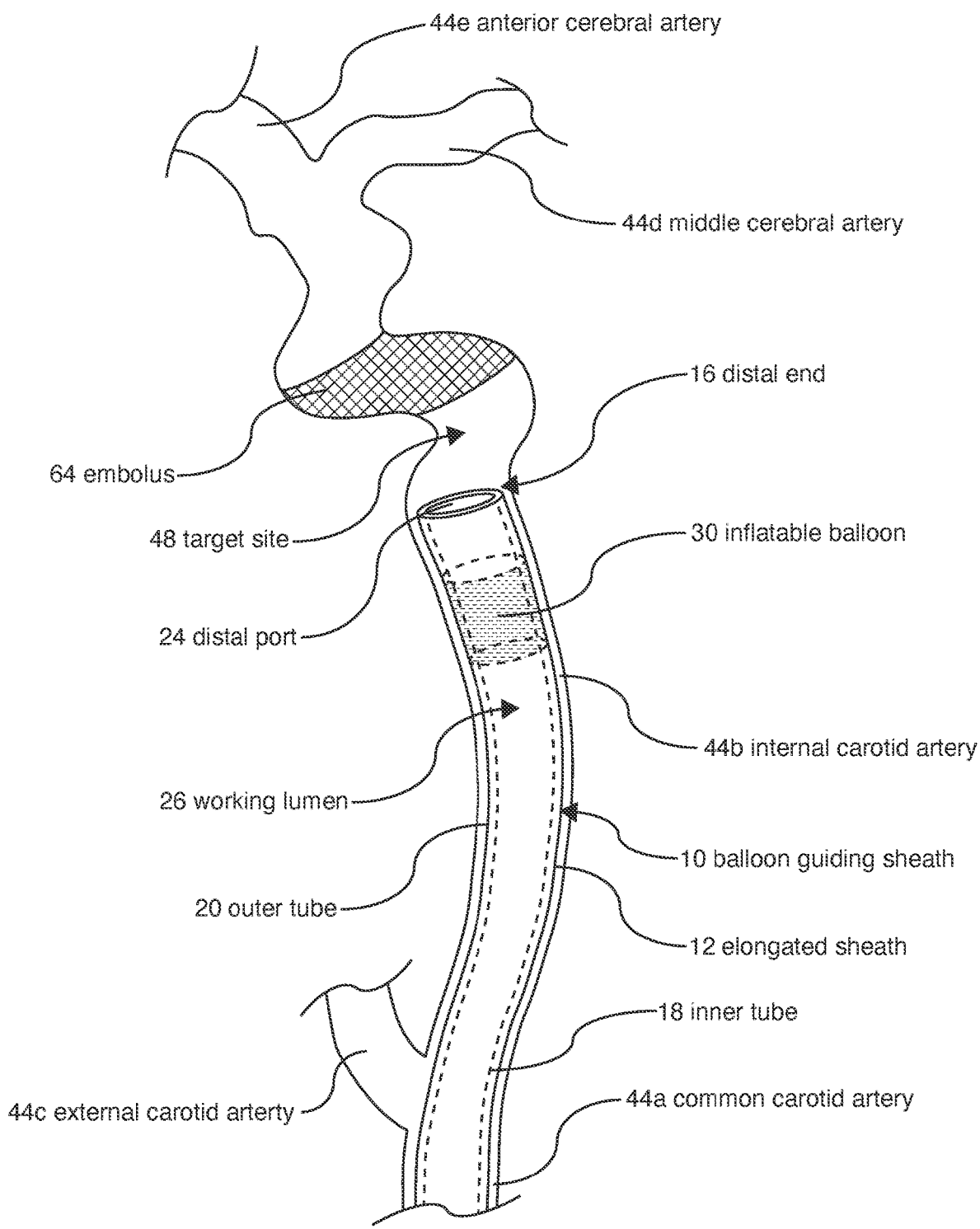
FIGS. 2 and 3 illustrate perspective views of a balloon guiding sheath, according to some embodiments.

As shown in FIGS. 1 and 2 and as will be discussed in greater detail later in the disclosure, in some embodiments the balloon guiding sheath 10 includes an inflatable balloon 30, which, in many embodiments, is located on an outer surface of an elongated sheath 12 and near a distal end of the elongated sheath 12. The balloon guiding sheath 10 may also include an access port 22 and an inflation port 36, both of which may be located near a proximal end of the elongated sheath 12. In some embodiments, the balloon guiding sheath 12 includes a distal port 24 located near a distal end of the elongated sheath 12.

FIG. 2 illustrates a perspective view of the balloon guiding sheath 10 located inside the vasculature 44. Specifically, FIG. 2 includes the common carotid artery ("CCA") 44a, which branches into the internal carotid artery ("ICA") 44b and the external carotid artery ("ECA") 44c. As shown, the middle cerebral artery ("MCA") 44d and the anterior cerebral artery ("ACA") 44e are located near a distal portion of the ICA 44b. FIG. 2 shows, in greater detail, the distal end 16 of the elongated sheath 12, including the distal port 24, located adjacent a target site 48. In many embodiments, the target site 48 is located adjacent an occlusion in a vessel, such as an embolus 64, as illustrated by FIG. 2. Occlusions, such as an embolus 64, are commonly located in the ICA 44b and near the MCA 44d, as shown in FIG. 2. As demonstrated by FIG. 1 as well as FIG. 2, the elongated sheath 12 may also include an inflatable balloon 30, which may be located adjacent the distal end 16. In some embodiments, the inflatable balloon 30 extends to a distal edge of the elongated sheath 12. The inflatable balloon 30 may also be located near, but not extend all the way to, the distal end 16, as illustrated in FIGS. 1 and 2.

In some embodiments, the inflatable balloon 30 is configured to inflate, thereby pausing a substantial amount of the blood flow through the vasculature 44 to the target site 48. Methods of inflating the balloon 30 will be discussed later in the disclosure. Once blood flow has been reduced and/or temporarily stopped, the balloon guiding sheath 10 may be configured to remove the embolus 64 through the distal port 24. Removal of the embolus 64 may be achieved through suction, as in an aspiration thrombectomy procedure, and/or with the use of an additional device that physically breaks up the embolus 64, as in a mechanical thrombectomy procedure. In some embodiments, the additional device is inserted through the access port 22 of the balloon guiding sheath 10, illustrated in FIG. 1.

FIG. 2 also shows that, in some embodiments, the balloon guiding sheath 10 includes an inner tube 18 and an outer tube 20. The outer tube 20 may substantially surround the inner tube 18, and both the inner and outer tubes 18, 20, may extend between the proximal end and the distal end 16 of the elongated sheath 12. The balloon guiding sheath 10 may also include a working lumen 26, which, in some embodiments, extends through an interior portion of the elongated sheath 12 between the distal port 24 and the access port 22. The working lumen 26 may be configured to enable removal of an embolus 64 by providing a passageway for suction and/or an additional device used for mechanical thrombectomy.

Figure 3:
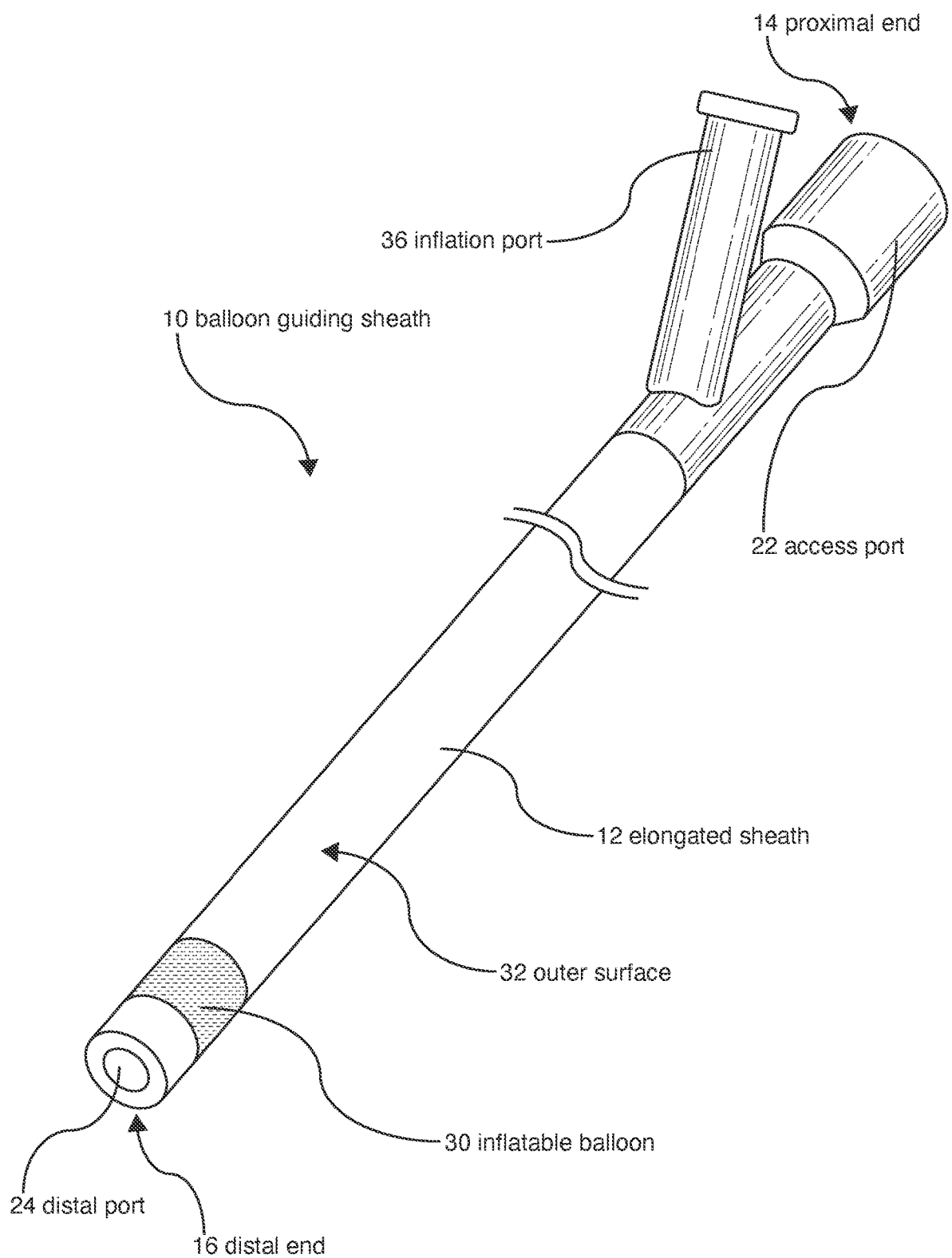

FIG. 3 illustrates another perspective view of the balloon guiding sheath 10, according to some embodiments. As shown, in some embodiments, the inflatable balloon 30 and the distal port 24 are located at and/or adjacent the distal end 16 and the access port 22 and inflation port 36 are located at and/or adjacent the proximal end 14. The inflation port 36 may be configured to enable inflation of the inflatable balloon 30. In some embodiments, inflation of the inflatable balloon 30 is achieved by the injection of at least one of fluid and media through the inflation port 36. The inflatable balloon 30 may be located on an outer surface 32 of the elongated sheath 12, and may wrap around substantially an entire circumference of the elongated sheath 12. Further details of the outer surface 32 will be discussed later in the disclosure, particularly with reference to FIGS. 6 and 7. In many embodiments, the elongated sheath defines a generally constant outer diameter from the proximal end 14 to the distal end 16. The balloon guiding sheath 10 may define a length of about ninety centimeters.

Figure 4A:
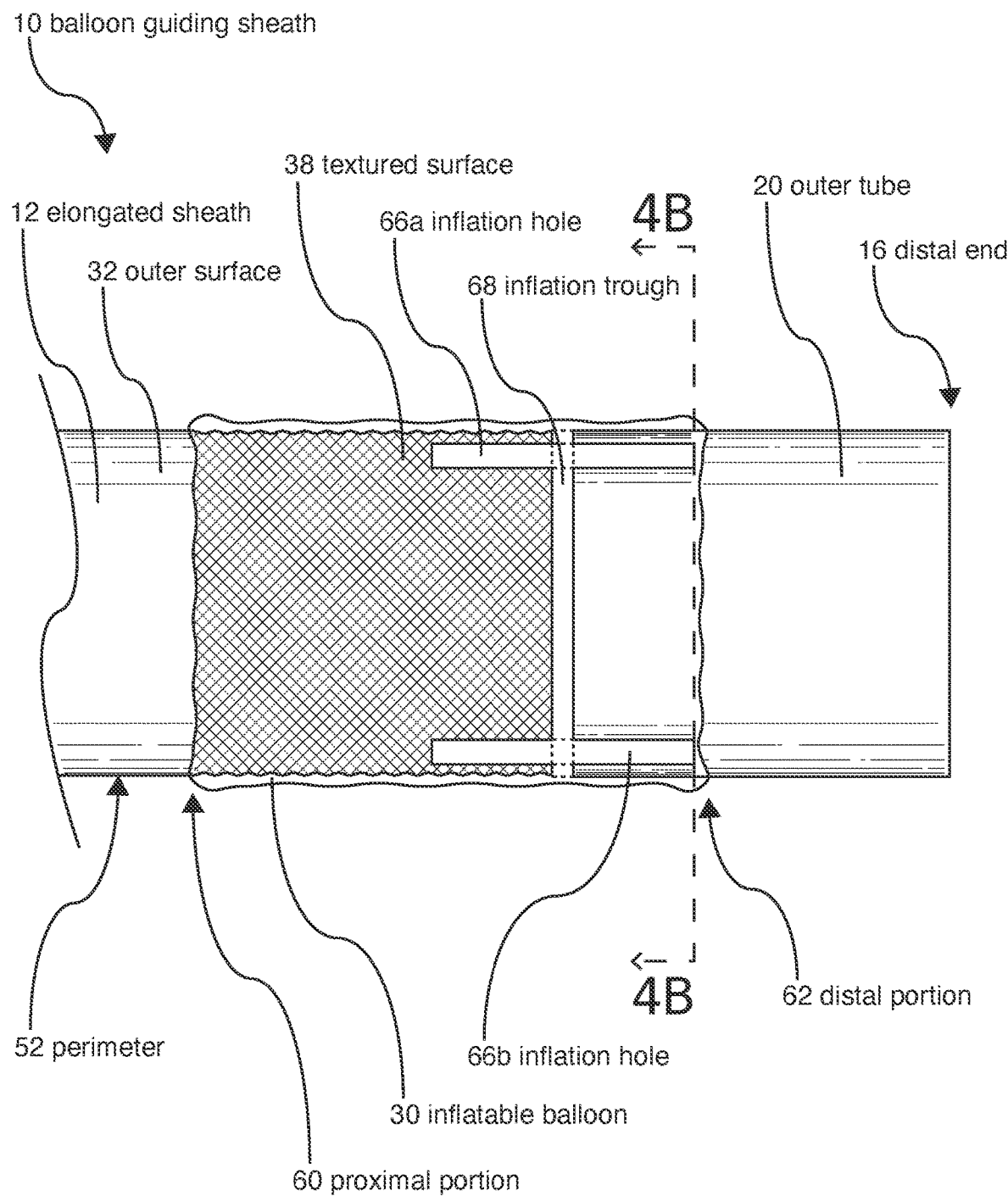
FIGS. 4A, 4B, 5A, 5B illustrate perspective views of a portion of a balloon guiding sheath including a textured surface, according to some embodiments.
Figure 4B:
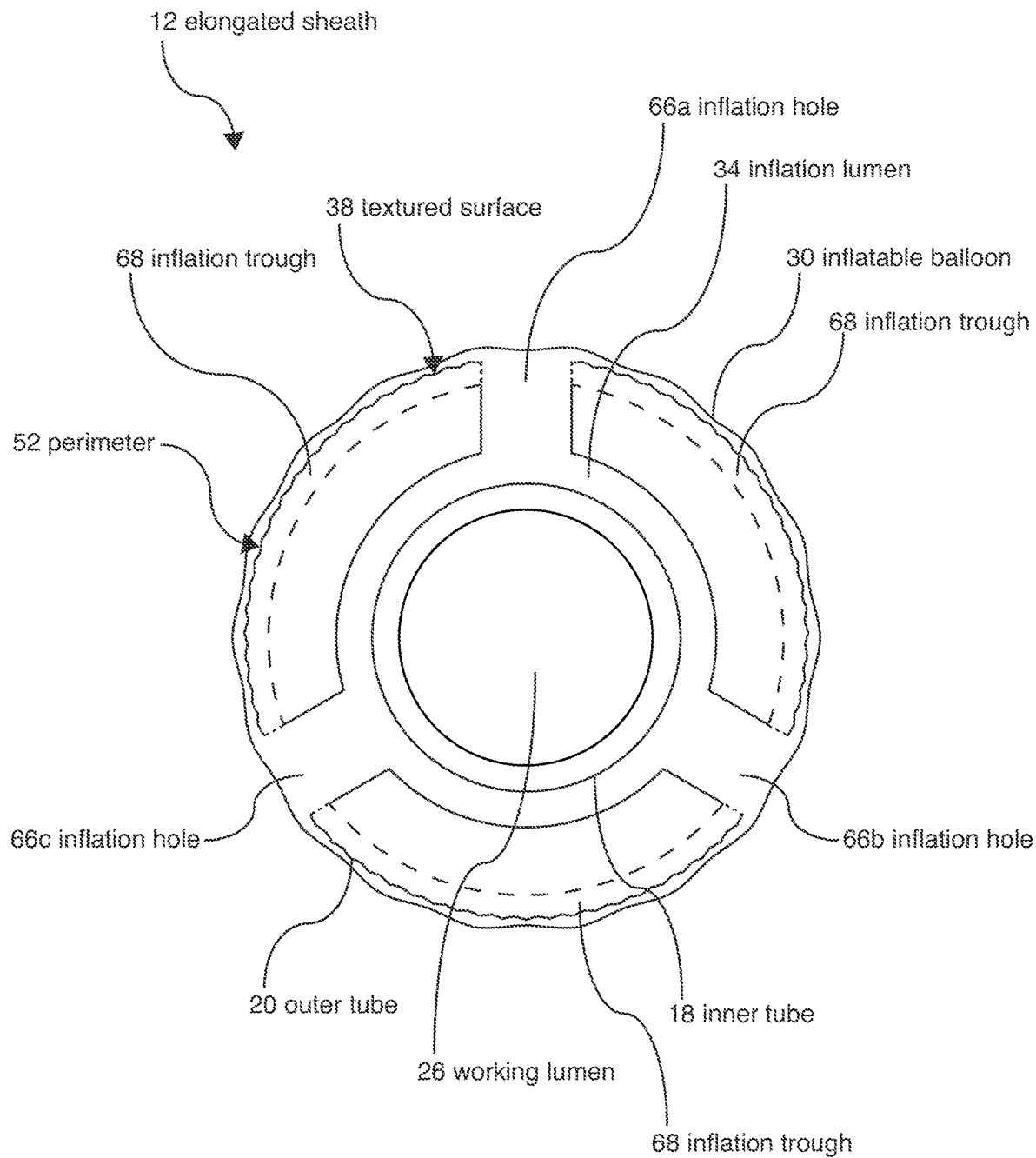
Figure 5A:
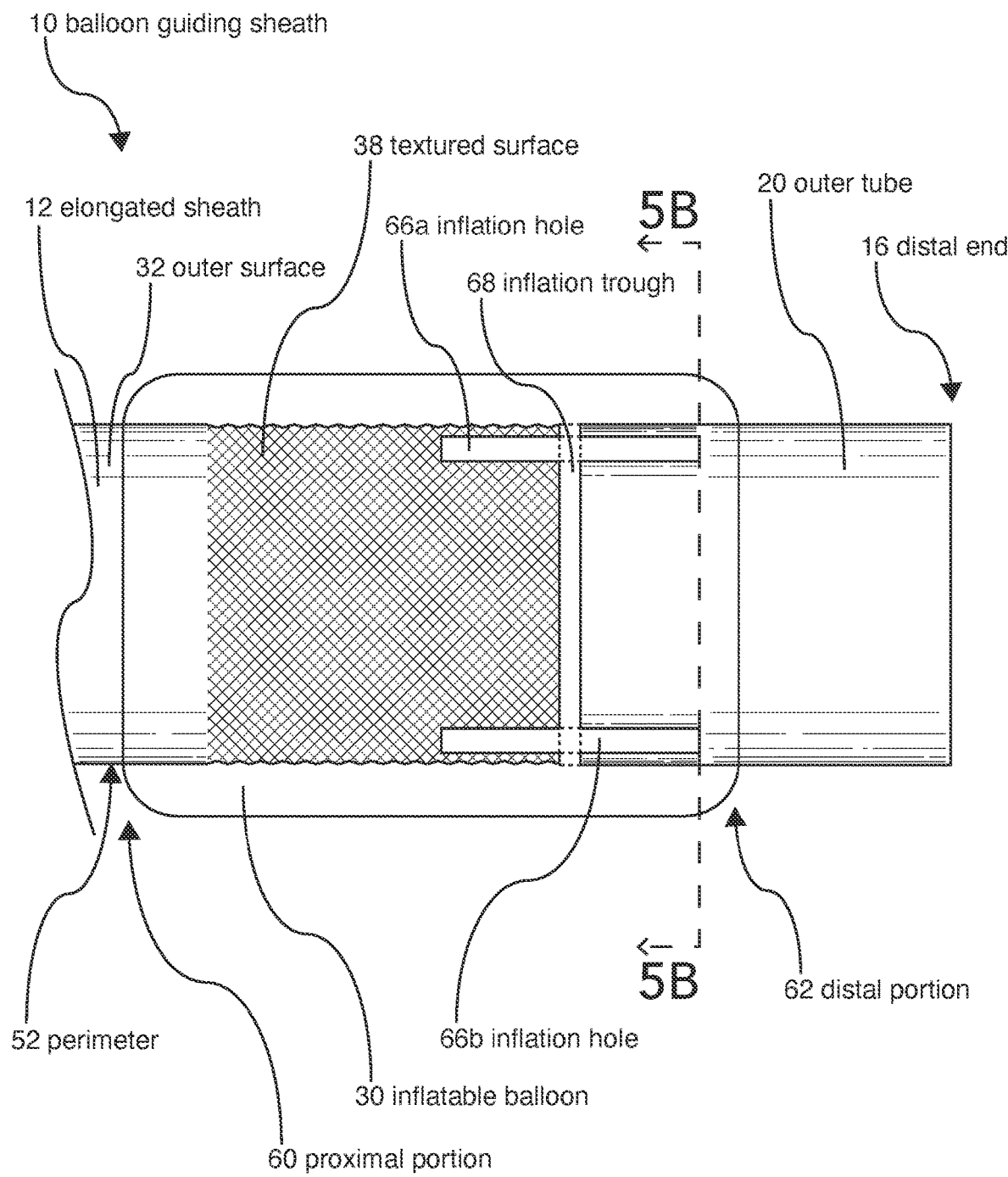

FIG. 4A illustrates a side view and FIG. 4B illustrates a cross-sectional view of the distal end 16 of the elongated sheath 12, according to some embodiments. The balloon guiding sheath 10 may also include an outer tube 20 and an inner tube 18, as illustrated in FIGS. 4B and 2. In many embodiments, the elongated sheath 12 includes a textured surface 38, as shown in FIG. 4A. In some embodiments, the textured surface 38 is located adjacent the distal end 16 of the elongated sheath 12. The textured surface 38 may be located along an outer surface 32 of the outer tube 20, and may also be located beneath the inflatable balloon 30, as shown in FIGS. 4A and 4B. For example, the textured surface may be defined by the outer surface 32 of the outer tube 20. In some examples, the textured surface 38 may be located closer to a proximal portion 60 than a distal portion 62 of the balloon 30, as indicated in FIGS. 4A and 5A. in addition, in some examples, the textured surface 38 may be located closer to the distal portion 62 than the proximal portion 60 of the balloon 30, or may be located substantially centrally between the proximal portion 60 and the distal portion 62.

In some embodiments, the textured surface 38 rotationally extends around at least a portion of a perimeter 52 of the outer tube 20. The textured surface 38 may rotationally extend about 360 degrees around an entire perimeter 52 of the outer tube 20. It should be noted that, due to the presence of at least one inflation hole 66 (discussed in more detail below), the perimeter 52 of the outer tube 20 may define less than 360 degrees. As such, the textured surface 38 may rotationally extend substantially the entire perimeter 52, which may be less than 360 degrees, as illustrated in FIGS. 4A and 4B. In some embodiments, the textured surface 38 is located between the inflatable balloon 30 and the inner tube 18. The inflatable balloon 30 may also extend between the inflatable balloon 30 and the outer tube 20.

Figure 5B:
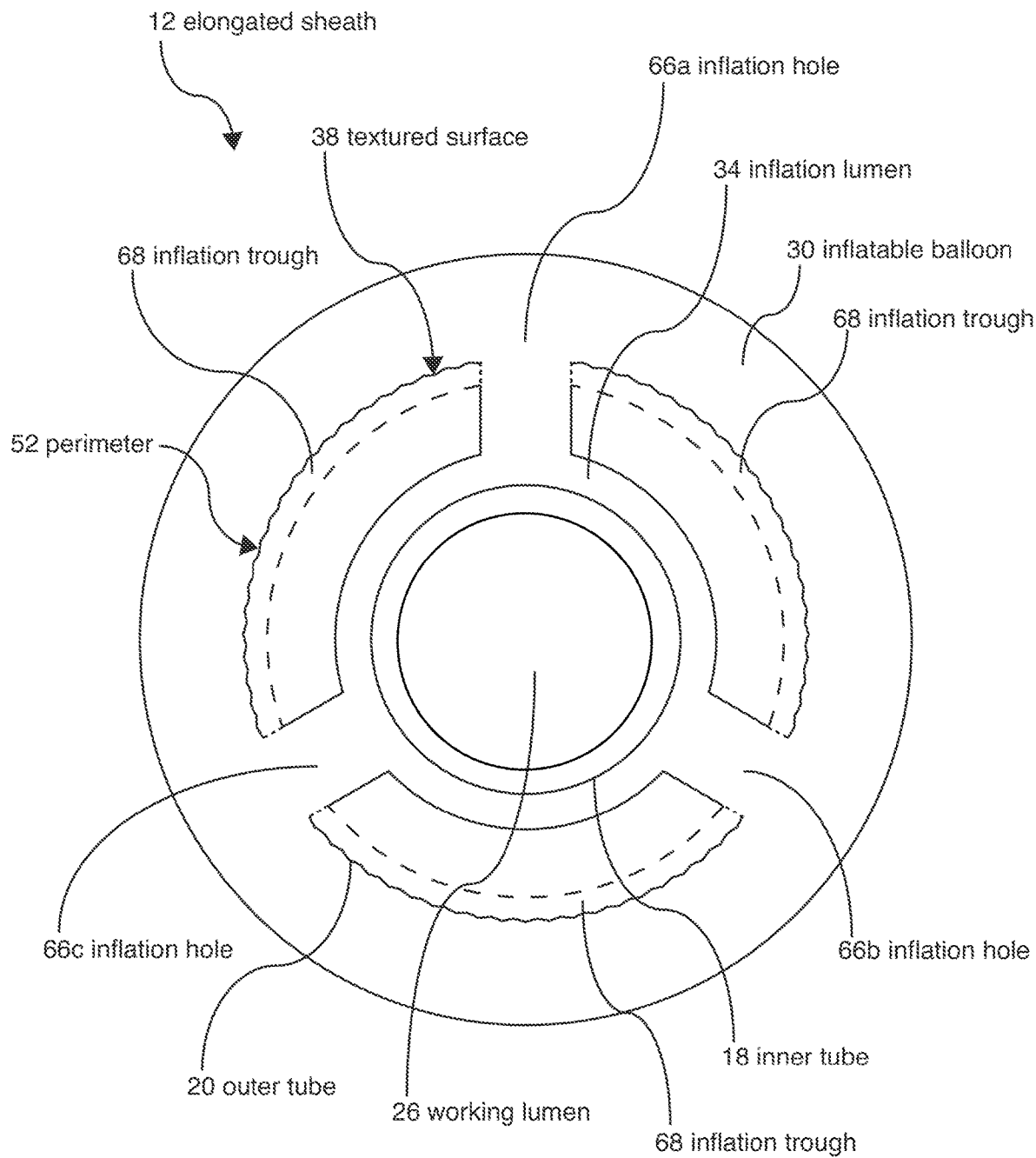

In many embodiments, the textured surface 38 is arranged and configured to reduce a contact area between the outer tube 20 and the inflatable balloon 30 when the inflatable balloon 30 is deflated, as illustrated in FIGS. 4A and 4B. The textured surface 38 may also be configured to reduce surface energy between the outer tube 20 and the inflatable balloon 30. Reducing at least one of a contact area and surface energy between the outer tube 20 and the inflatable balloon 30 (when the balloon 30 is deflated) may assist in achieving substantially symmetrical inflation of the inflatable balloon 30, as illustrated in FIGS. 5A and 5B. It should be noted that "symmetrical inflation" is intended to indicate radial symmetry of the inflated balloon 30. As such, when inflated in a "substantially symmetrical" manner, the inflatable balloon 30 comprises a substantially consistent diameter from a proximal portion to a distal portion of the balloon 30.

In some embodiments, the inflatable balloon 30 comprises a thermoplastic material with high surface energy that may be prone to adhering, such as via solvent bonding, to the outer tube 20. When the balloon 30 adheres to the outer tube 20, it may be difficult to achieve even inflation of the outer balloon 30 as portions of the balloon 30 may remain bonded to the outer tube 20 even after inflation. Minimizing the energy and/or contact area between the outer tube 20 and the inflatable balloon 30 (when the balloon 30 is deflated) may reduce the opportunities for bonding between the tube 20 and the balloon 30. In many embodiments, minimizing the surface energy and/or contact area between the outer tube 20 and the inflatable balloon 30 (when the balloon 30 is deflated) is achieved through the implementation of the textured surface 38.

In many embodiments, the balloon guiding sheath 10 comprises an inflation lumen 34 that extends between the inner tube 18 and the outer tube 20, as demonstrated in FIG. 4B, and from the inflation port 36 to the inflatable balloon 30. The inflation lumen 34 may be configured to carry the at least one of fluid and media from the inflation port 36, shown in FIGS. 1 and 3, to the inflatable balloon 30, thereby enabling inflation of the inflatable balloon 30. The fluid coupling between the inflation lumen 34 and the inflatable balloon 30 may also enable deflation of the balloon 30 by withdrawing the at least one of fluid and media from the balloon 30, through the inflation lumen 34, and out through the inflation port 36. FIGS. 4A and 4B show the inflatable balloon 30 in a deflated state.

FIGS. 4A and 4B also include an inflation trough 68 and at least one inflation hole 66a, 66b, 66c. In many embodiments, the inflatable balloon 30 is configured to inflate in a substantially symmetrical manner. The inflatable balloon 30 may also inflate in an asymmetrical manner. As previously discussed, the inflation lumen 34 may be configured to carry at least one of fluid and media from the inflation port 36 to the inflatable balloon 30. In many embodiments, the fluid and/or media flows through at least one inflation hole 66a, 66b, 66c. In this manner, the inflation holes 66 may be configured to fluidly couple the inflation lumen 34 and the inflatable balloon 30. The elongated sheath 12 may comprise a plurality of inflation holes 66 located adjacent the distal port 24. In some embodiments, and as illustrated by FIG. 4B, the elongated sheath 12 comprises three inflation holes substantially evenly spaced around, and extending through, a side wall of the elongated sheath 12. The side wall may be the outer tube 20. The elongated sheath 12 may comprise three inflation holes 66 substantially symmetrically spaced around the outer tube 20 of the elongated sheath 12. The elongated sheath 12 may comprise a number other than three inflation holes 66, which may be substantially evenly spaced from one another.

In many embodiments, each inflation hole 66a, 66b, 66c of the plurality of inflation holes 66 are configured to fluidly couple to one another via at least one of the inflation lumen 34 and an inflation trough 68. The plurality of inflation holes 66 may also be configured to fluidly couple the inflation lumen 34 to the inflation trough 68. In some embodiments, the inflation trough 68 is located between the inflatable balloon 30 and the outer tube 20. The inflation trough 68 may be thought of as an "etched out" layer of the outer tube 20. The inflation trough 68 may also be located on the outer tube 20. Fluid coupling between each inflation hole 66a, 66b, 66c of the plurality of inflation holes 66 may allow at least one of fluid and media to flow around the inflation trough 68 in order to maintain substantially even and substantially constant pressure and/or inflation of the inflatable balloon 30.

In some embodiments, the inflation trough 68 rotationally extends around at least a portion of a perimeter 52 of the outer tube 20 in order to fluidly couple at least two inflation holes 66a, 66b, 66c of the plurality of inflation holes 66. The inflation trough 68 may rotationally extend about 360 degrees around the perimeter 52 of the outer tube 20 in order to fluidly couple each inflation hole 66a, 66b, 66c of the plurality of inflation holes 66. In some embodiments, the elongated sheath 12 is elongate along a first direction and the inflation trough 68 rotationally extends along a second direction that is perpendicular to the first direction. As such, the inflation trough 68 may extend radially out from the outer tube 20 in a direction perpendicular to the elongate direction of the elongated sheath. In some embodiments, the inflation trough 68 defines a depth radially extending along the second direction that is perpendicular to the first direction. The depth may be about 0.002 inches. In some embodiments, the inflation trough 50 defines a depth of 0.002 inches radially extending from an outer edge of the elongated sheath 12 toward the working lumen 26. The inflation trough 50 may define a depth of about 0.001 inches.

In some embodiments, the inflation holes 38 are elongate along the first direction, such that the elongated sheath 12 is elongate along the same direction as the inflation holes 38. Similar to the inflation trough 50, the at least one inflation hole 38 may define a depth radially extending from an outer edge of the elongated sheath 12 radially inward toward the working lumen 26. In some embodiments, the depth is 0.01 inches. The depth may be about 0.01 inches. In some embodiments, the depth of the inflation holes 38 is 0.005 inches.

Referring now to FIGS. 5A and 5B, it should be noted that FIGS. 5A and 5B are similar to FIGS. 4A and 4B, respectively, but FIGS. 5A and 5B show the inflatable balloon 30 in an inflated state. As previously discussed, in many embodiments, the balloon 30 is configured to inflate in a substantially symmetrical manner such that the inflatable balloon 30 achieves radially symmetry and defines a generally consistent diameter from a proximal portion to a distal portion. FIGS. 5A and 5B demonstrate such substantially symmetrical inflation. In many embodiments, the textured surface 38 aids in achieving substantially symmetrical inflation by reducing at least one of surface contact and surface energy between the outer tube 20 and the inflatable balloon 30 (when the balloon 30 is in a deflated state), thus reducing the chance of at least part of the balloon 30 adhering to the outer tube 20, which would compromise symmetrical inflation. As previously discussed, the inflation holes 66 and inflation trough 68 may also help facilitate substantially symmetrical inflation of the balloon 30. In some embodiments, the inflatable balloon 30 is configured to inflate in an asymmetrical manner.

Figure 6A:
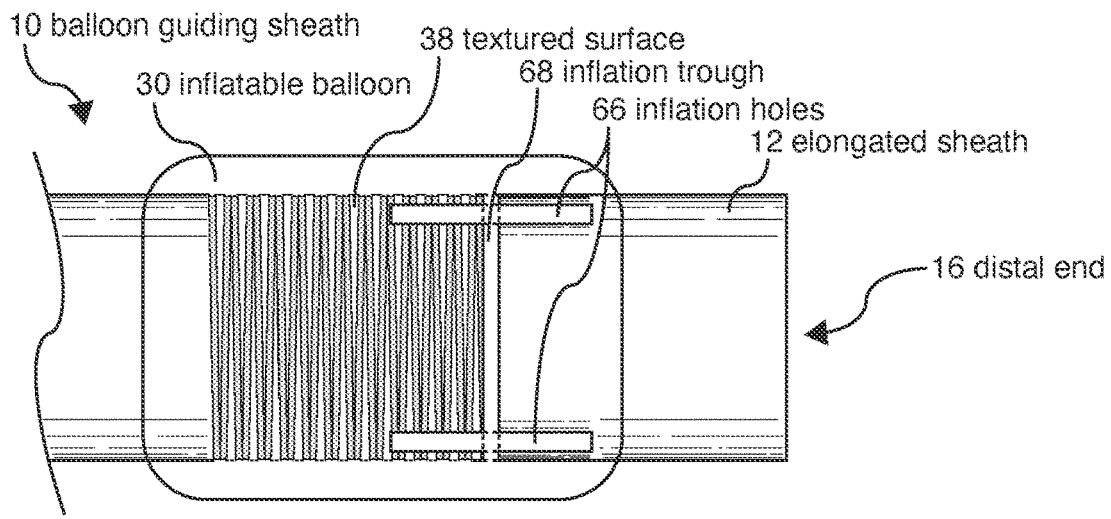
FIGS. 6A, 6B, and 6C illustrate side views of a portion of a balloon guiding sheath including a textured surface, according to some embodiments.
Figure 6B:
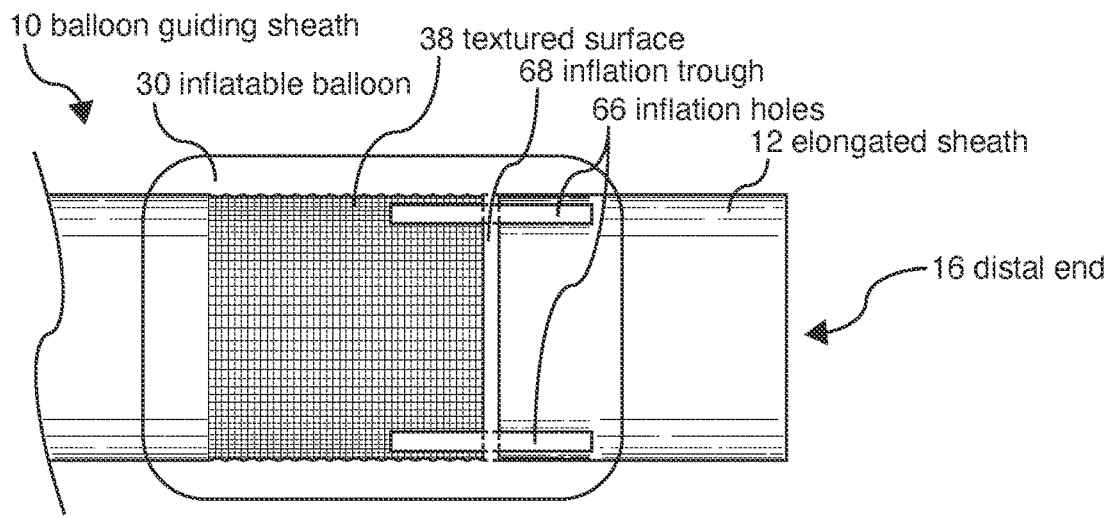
Figure 6C:
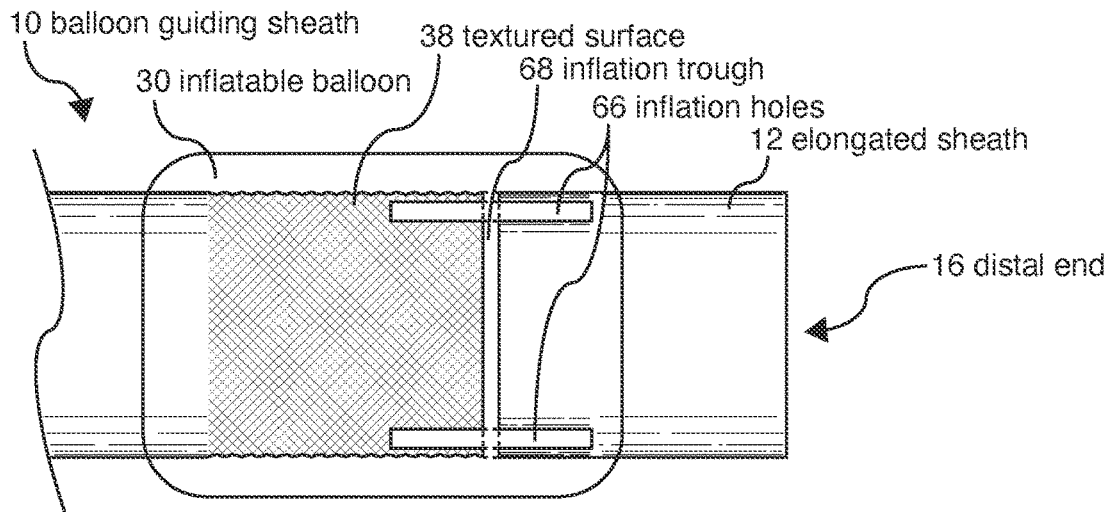

FIGS. 6A-6C illustrate different embodiments of a balloon guiding sheath 10 comprising a textured surface 38. As shown in FIGS. 6A-6C, the textured surface 38 may define different surfaces. In many embodiments, a variety of textures are suitable to reduce surface contact/surface tension between the outer tube 20 and the inflatable balloon 30 (when the balloon 30 is deflated). For example, the textured surface 38 may define even cross-hatching or a similar pattern, as demonstrated by FIGS. 6B and 6C. The textured surface 38 may also define a more irregular texture, as illustrated in FIG. 6A. In some embodiments, the textured surface 38 defines a cross-sectional profile defining a rectangular shape. The textured surface 38 may define a cross-sectional profile defining a triangular shape. The cross-sectional profile may define any suitable shape to reduce at least one of surface contact and surface energy between the outer tube 20 and the inflatable balloon 30 when the balloon 30 is in a deflated position.

Figure 7A:
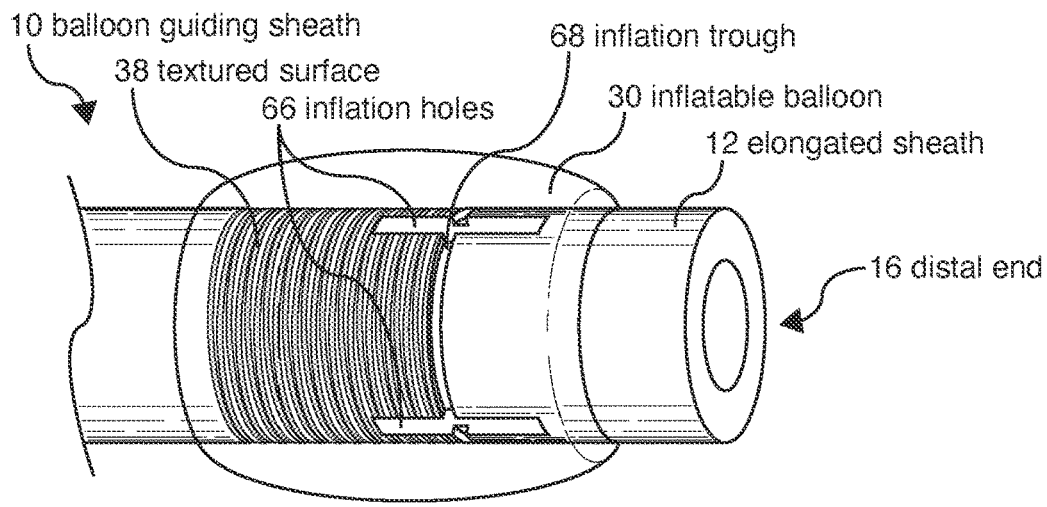
FIGS. 7A, 7B, and 7C illustrate isometric views of a distal portion of a balloon guiding sheath, according to some embodiments.
Figure 7B:
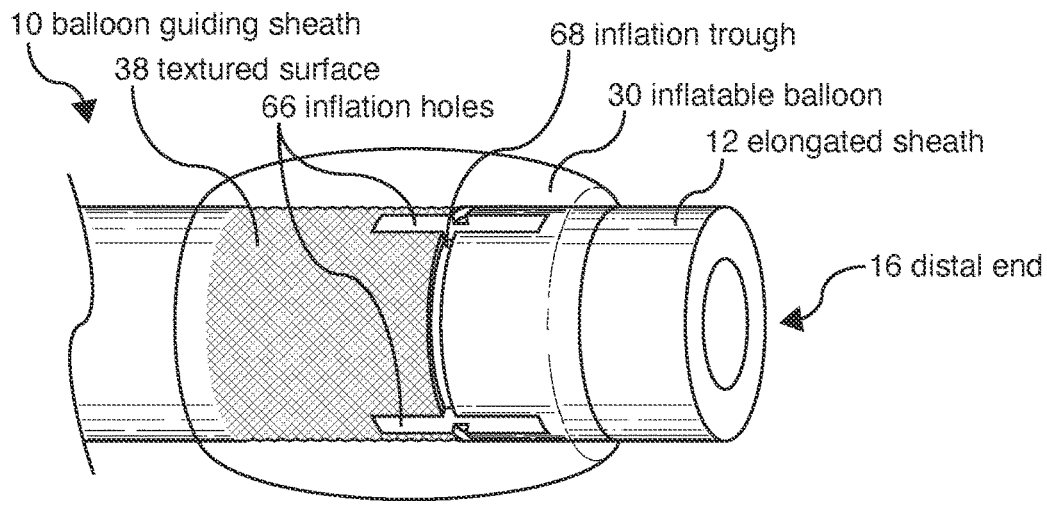
Figure 7C:
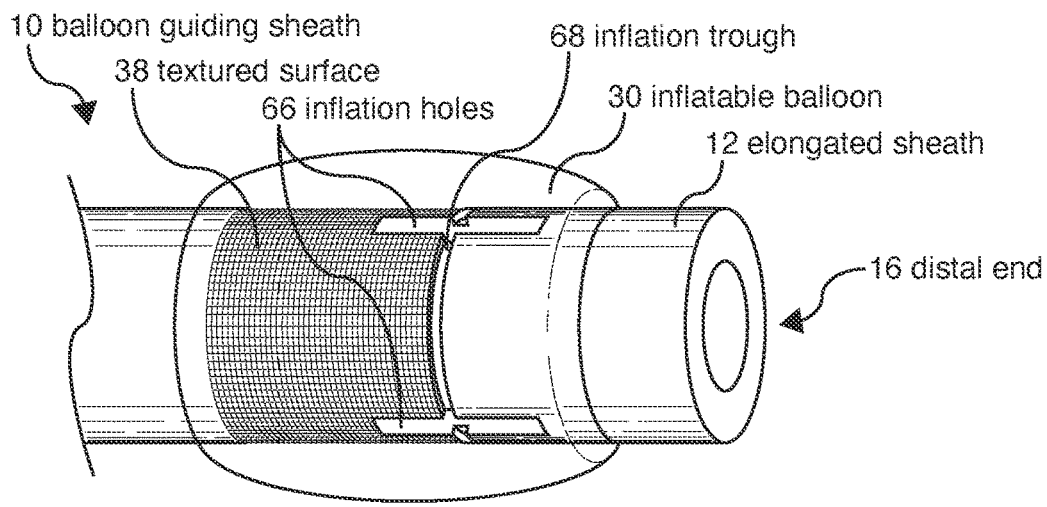

FIGS. 7A-7C are similar to FIGS. 6A-6C, respectively, but illustrate an isometric view rather than a side view of a distal portion of the elongated sheath 12. As shown in FIGS. 6A-7C, in some embodiments, the textured surface 38 defines a first area and the inflatable portion of the inflatable balloon 30 defines a second area, wherein the second area is greater than the first area. As such, less than the entire surface contact area between the outer tube 20 and the inflatable balloon 30 may include the textured surface 38. It should be noted that the textured surface 38 may cover more or less of the outer tube 20 than shown in FIGS. 6A-7C. Even still, the textured surface 38 may be substantially entirely located beneath the inflatable balloon 30. As discussed with reference to FIGS. 4A and 5A, and as shown in FIGS. 6A-7C, in many embodiments, the textured surface 38 is located closer to a proximal portion 60 (not labeled in FIGS. 6A-7C) than a distal portion 62 (not labeled in FIGS. 6A-7C) of the inflatable balloon 30. The textured surface 38 may also be located closer to the distal portion 62 than the proximal portion 60 of the balloon 30, or may be located substantially centrally between the proximal portion 60 and the distal portion 62.

FIGS. 4A, 5A, and 6A-7C also demonstrate that, unlike the location of the textured surface 38, the inflation trough 68 and inflation holes 66 may be located closer to a distal portion 62 of the inflatable balloon 30 than to a proximal portion 60 of the balloon 30. In many embodiments, the distal portion 62 of the inflatable balloon 30 is located adjacent the distal end 16 of the elongated sheath 12, such that the inflation trough 68 and the at least one inflation hole 66 are located adjacent the distal end 16 of the elongated sheath 12.

Figure 8A:
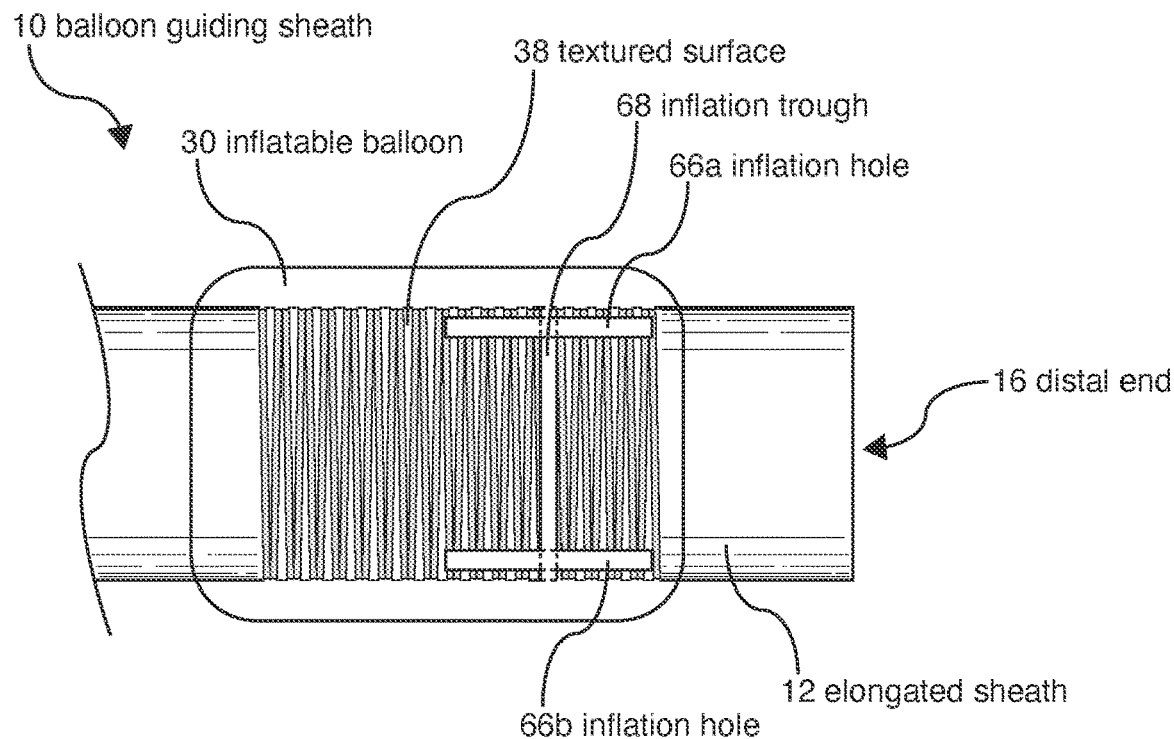
FIGS. 8A, 8B, 8C, 8D, and 8E illustrate side views of a balloon guiding sheath including a textured surface and at least one inflation hole, according to some embodiments.

FIGS. 8A-8E illustrate different embodiments of the balloon guiding sheath 10 including inflation hole(s). As shown in FIG. 8A, in some embodiments, the sheath 10 includes at least two inflation holes 66a, 66b and an inflation trough 68 extending between the inflation holes 66a, 66b. FIG. 8A illustrates a similar embodiment to that shown in, and discussed with reference to, the other Figures of this disclosure. FIG. 8A also shows that the textured surface 38 may be located closer to a distal portion 62 than a proximal portion 60 of the inflatable balloon 30. It should be noted that the textured surface 38 may be located closer to either end of the balloon 30, or may extend substantially the full length of the balloon 30.

Figure 8B:
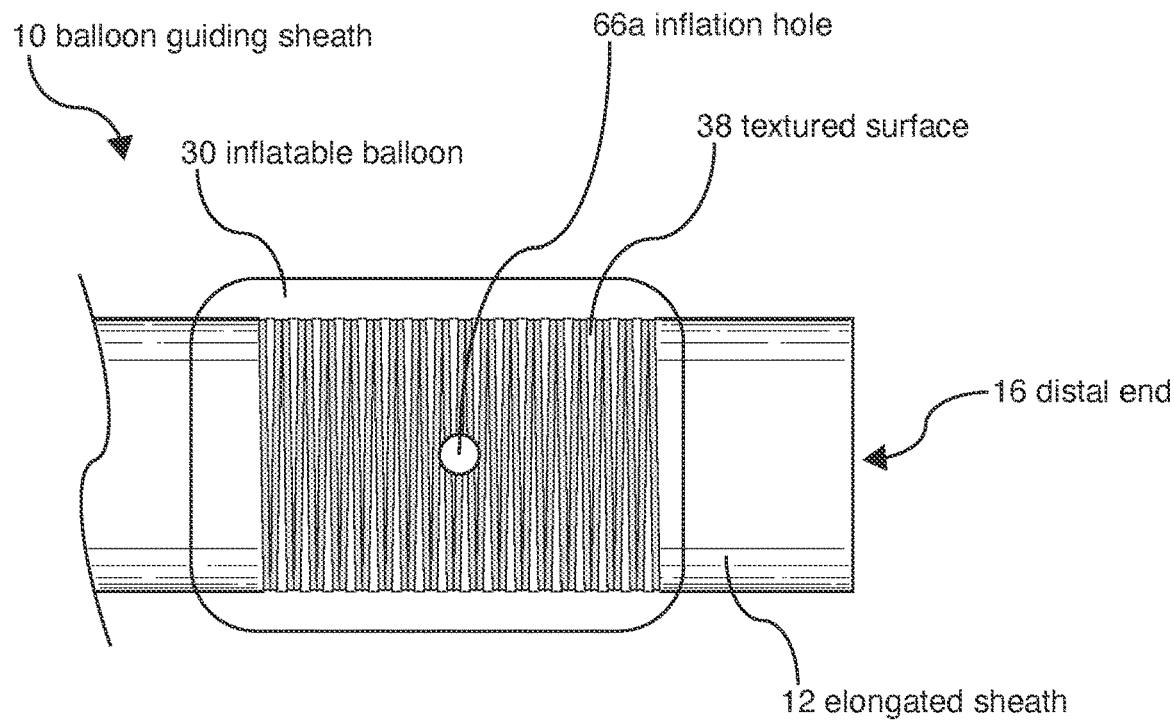
Figure 8C:
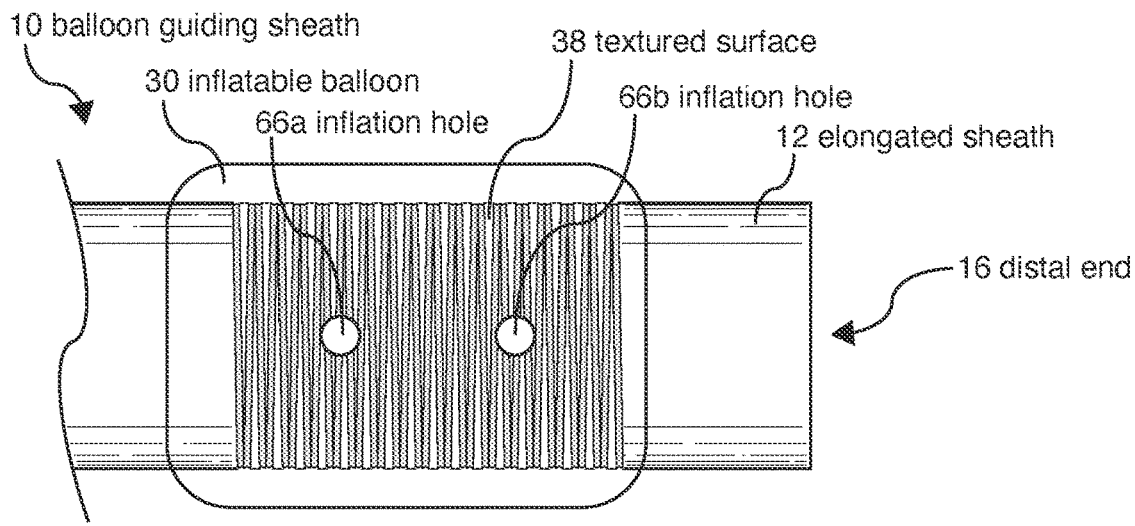
Figure 8D:
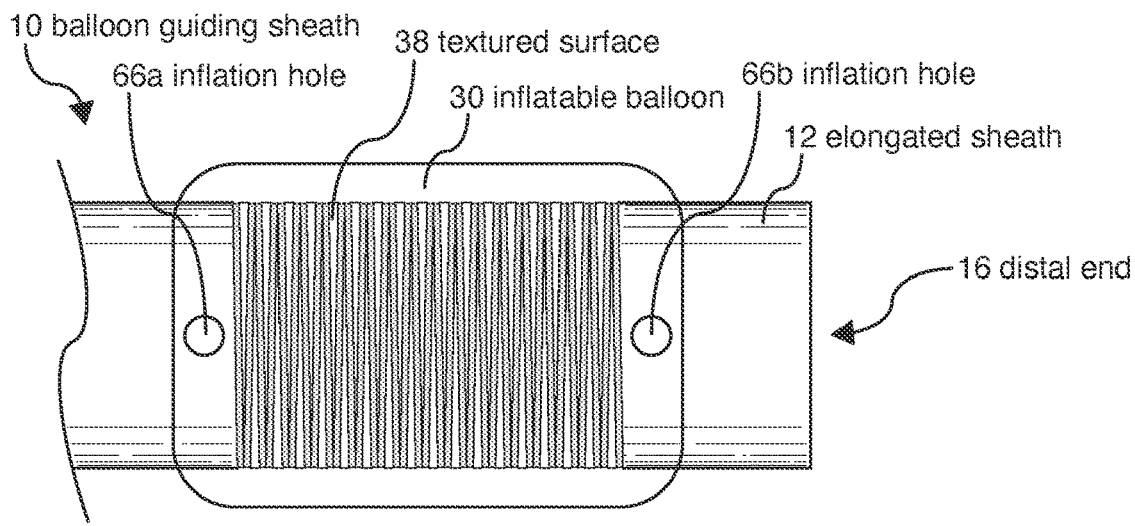
Figure 8E:
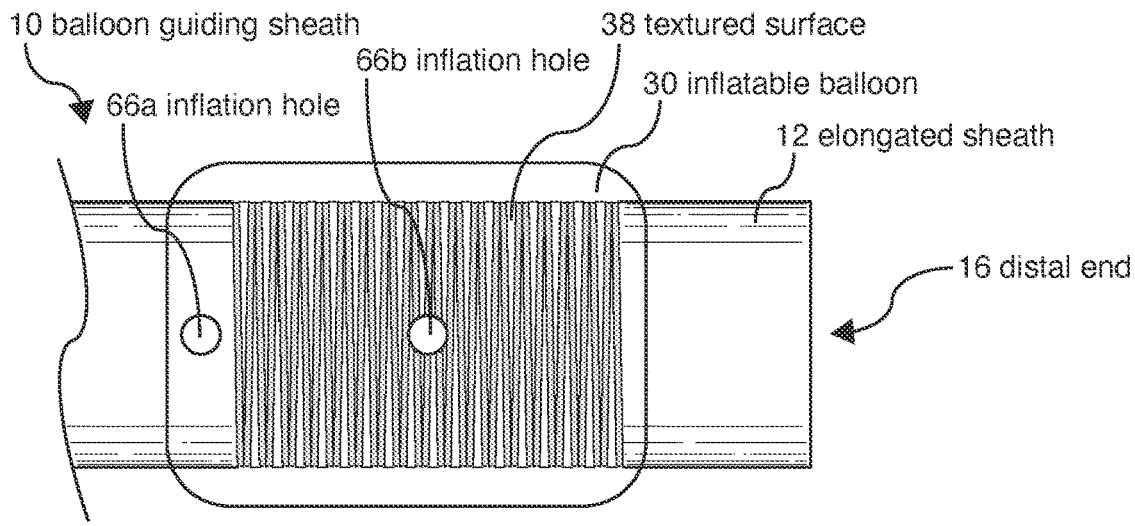

FIG. 8B shows an embodiment of the balloon guiding sheath 10 comprising a single inflation hole 66a located substantially centrally on the textured surface 38 of the elongated sheath 12. The single inflation hole 66a may be located anywhere on the textured surface 38. FIGS. 8C-8E each illustrate embodiments including two inflation holes 66a, 66b. FIG. 8C shows the inflation holes 66a, 66b substantially evenly spaced from one another on top of the textured surface 38. FIG. 8D illustrates the inflation holes 66a, 66b located beneath the inflatable balloon 30 at opposite ends of the balloon 30, and not on top of the textured surface 38. FIG. 8E demonstrates that, in some embodiments, the balloon guiding sheath 10 includes one inflation hole 66b located on the textured surface 38 and one inflation hole 66a not located on the textured surface 38. It should be noted that FIGS. 8A-8E show only some of the possible embodiments of the placement of inflation hole(s) on the elongated sheath 12. A number of other suitable variations are possible, including but not limited to, embodiments with no inflation holes 66, embodiments with three or more inflation holes 66, and embodiments where multiple inflation holes 66 are not evenly spaced from one another and/or are located at different locations on the elongated sheath 12 than demonstrated in FIGS. 8A-8E.

Figure 9A:
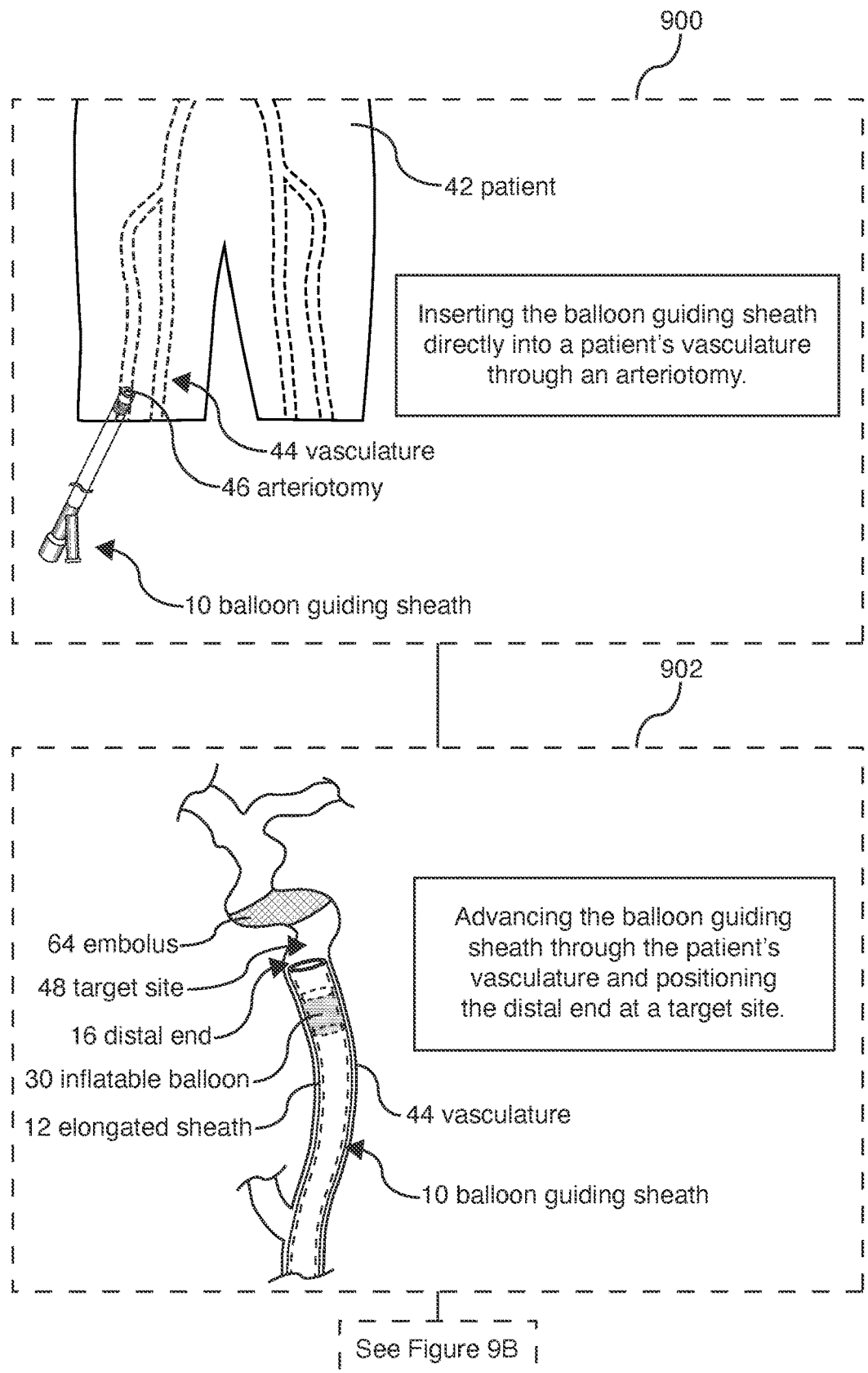
FIGS. 9A and 9B illustrate a method of using a balloon guiding sheath, according to some embodiments.
Figure 9B:
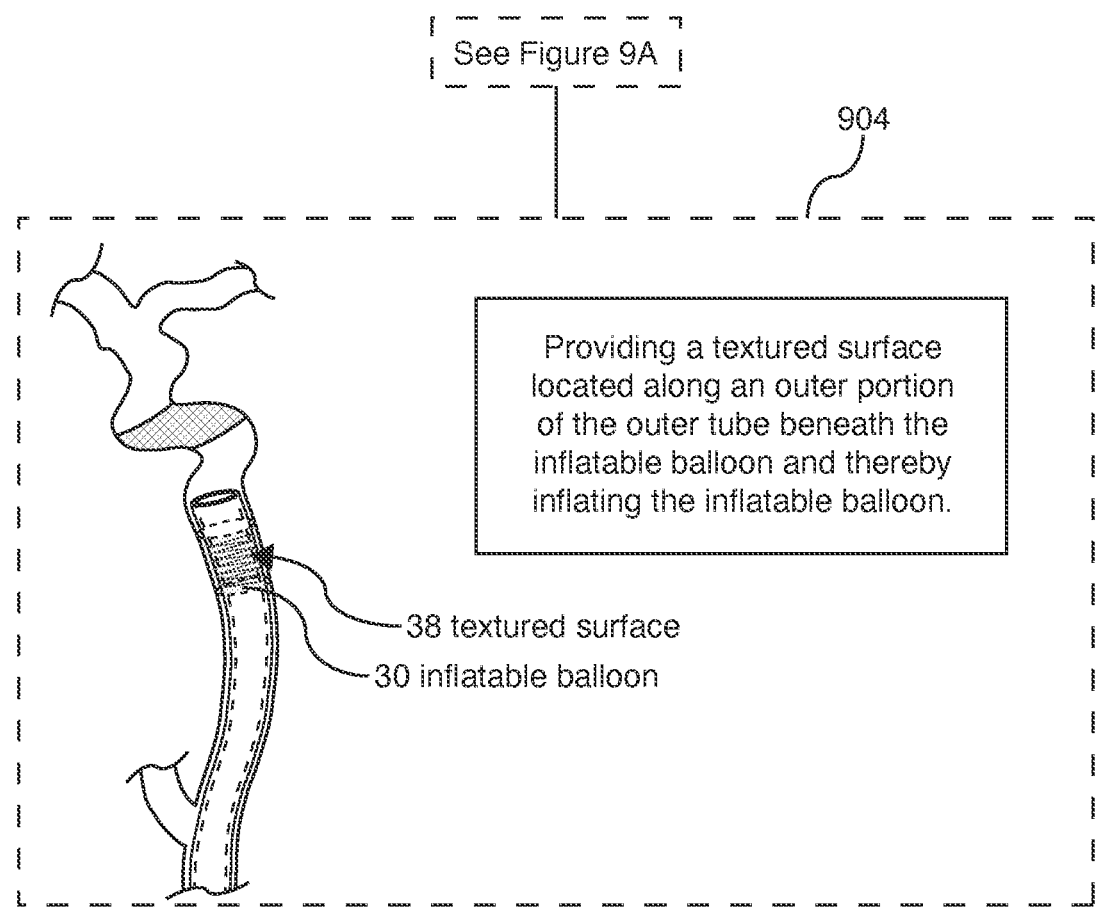

FIGS. 9A and 9B illustrate a method of using the balloon guiding sheath 10, according to some embodiments. As shown by step 900 of FIG. 9A, in some embodiments, the method comprises inserting the balloon guiding sheath 10 directly into a patient's 42 vasculature 44 through an arteriotomy 46. As previously mentioned, the arteriotomy 46 may be located in a variety of arteries of a patient 42, including but not limited to: a femoral artery, a vertebral artery, and a radial artery. FIG. 9A demonstrates the arteriotomy 46 located in the thigh of the patient 42 to enable femoral access into the vasculature 44. Step 902 shows that the method may further comprise advancing the balloon guiding sheath 10 through the patient's 42 vasculature 44 and positioning the distal end 16 at a target site 48. As discussed with reference to FIG. 2, in some embodiments the target site 48 is located adjacent an embolus 64 in the ICA 44b, such that when the balloon guiding sheath 10 is located at the target site 48, the sheath 10 is in position to remove the embolus 64.

FIG. 9B, at step 904, illustrates providing a textured surface 38 located along an outer portion of the outer tube 20 beneath the inflatable balloon 30 and thereby inflating the inflatable balloon 30. Inflating the inflatable balloon 30 may comprise inflating the balloon 30 with at least one of fluid and media via the plurality of inflation holes 66 and the inflation trough 68. In some embodiments, inflating the balloon 30 comprises substantially symmetrically inflating the balloon. The inflatable balloon 30 may also be inflated in an asymmetrical manner. In order to achieve substantially symmetrical inflation, the method may comprise applying a substantially even inflation force into the inflatable balloon 30 via the plurality of inflation holes 66 and the inflation trough 68. In some embodiments, the inflation force radially extends around a perimeter 52 of the elongated sheath 12, and the inflation force is directed away from the elongated sheath 12 to thereby substantially symmetrically inflate the inflatable balloon 30 with radial symmetry. The method may also comprise maintaining a substantially constant and even pressure within the inflatable balloon 30 in order to maintain even inflation.

As previously discussed, substantially symmetrical inflation may also be achieved by the textured surface 38 reducing at least one of the contact area and surface energy between the outer tube 20 and the inflatable balloon 30 when the balloon 30 is at least in a partially deflated position (state or condition). In response to reducing the surface contact between the inflatable balloon 30 and the outer tube 20, the method may comprise substantially symmetrically inflating the inflatable balloon 30. In response to reducing the surface contact between the outer tube 20 and the inflatable balloon 30 when the balloon 30 is in an uninflated state, the method may further comprise substantially symmetrically separating the inflatable balloon 30 from the textured surface 38. In response to reducing the surface energy between the inflatable balloon 30 and the outer tube 20, the method may comprise substantially symmetrically inflating the inflatable balloon 30. In response to reducing the surface energy between the inflatable balloon 30 and the outer tube 20, the method may also comprise substantially symmetrically separating the inflatable balloon 30 from the textured surface 38.

In some embodiments, while inflating the inflatable balloon 30, the method comprises maintaining a location of the distal end 16 of the elongated sheath 12 such that the distal end 16 is substantially located in the first position adjacent the target site 48, as illustrated in step 802 of FIG. 8A. After the inflating, the method may comprise continuing to maintain the location of the distal end 16 of the elongated sheath 12 such that the distal end 16 is still substantially located in the first position after inflating the inflatable balloon 30.

In some embodiments, the method further comprises flowing at least one of fluid and media over the textured surface 38 in order to achieve inflation of the balloon 30. As previously discussed, in many embodiments, the inflating comprises injecting, via the inflation port 36, at least one of fluid and media into the inflation lumen 34, over the textured surface 38, through at least one inflation hole 66 and the inflation trough 68, and into the inflatable balloon 30. In some embodiments, the elongated sheath 12 is elongate along a first direction and the inflation trough 68 defines a depth radially extending along a second direction that is perpendicular to the first direction. The inflating may comprise sending the at least one of fluid and media through the inflation lumen 34 along the first direction, sending the at least one of fluid and media through the plurality of inflation holes along the second direction, sending the at least one of fluid and media through the inflation trough 68 rotationally around the outer tube 20, and sending the at least one of fluid and media radially along the second direction away from the elongated sheath 12 to thereby inflate the inflatable balloon 30.

It should be noted that the components of the balloon guiding sheath 10 may be formed of any suitable material including, but not limited to, hard and/or soft polymer plastics, rubber, metallic materials, and any combination thereof. Any biocompatible material that may be structurally suitable may be used to form any component or components of the balloon guiding sheath 10. The fluid and/or media used to inflate the inflatable balloon 30 may comprise saline or a similar solution. In the event suction is used to remove an embolus 64, an external vacuum force may be applied to the distal end 16 of the elongated sheath 12, such as to the access port 22. The inflatable balloon 30 may comprise one layer or may comprise a plurality of layers. The textured surface 38 may be scratched/etched onto the outer tube 20 and/or added on top of the outer tube 20, such as through the use of additional material adhered to the tube 20. In some embodiments, the elongated sheath 12 has a degree of flexibility to allow a user (i.e. a medical professional) to maneuver the balloon guiding sheath 10 through the vasculature 44 of a patient 42.

Interpretation

None of the steps described herein is essential or indispensable. Any of the steps can be adjusted or modified. Other or additional steps can be used. Any portion of any of the steps, processes, structures, and/or devices disclosed or illustrated in one embodiment, flowchart, or example in this specification can be combined or used with or instead of any other portion of any of the steps, processes, structures, and/or devices disclosed or illustrated in a different embodiment, flowchart, or example. The embodiments and examples provided herein are not intended to be discrete and separate from each other.

The section headings and subheadings provided herein are nonlimiting. The section headings and subheadings do not represent or limit the full scope of the embodiments described in the sections to which the headings and subheadings pertain. For example, a section titled "Topic 1" may include embodiments that do not pertain to Topic 1 and embodiments described in other sections may apply to and be combined with embodiments described within the "Topic 1" section.

To increase the clarity of various features, other features are not labeled in each figure.

The various features and processes described above may be used independently of one another, or may be combined in various ways. All possible combinations and subcombinations are intended to fall within the scope of this disclosure. In addition, certain method, event, state, or process blocks may be omitted in some implementations. The methods, steps, and processes described herein are also not limited to any particular sequence, and the blocks, steps, or states relating thereto can be performed in other sequences that are appropriate. For example, described tasks or events may be performed in an order other than the order specifically disclosed. Multiple steps may be combined in a single block or state. The example tasks or events may be performed in serial, in parallel, or in some other manner. Tasks or events may be added to or removed from the disclosed example embodiments. The example systems and components described herein may be configured differently than described. For example, elements may be added to, removed from, or rearranged compared to the disclosed example embodiments.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require at least one of X, at least one of Y, and at least one of Z to each be present.

The term "and/or" means that "and" applies to some embodiments and "or" applies to some embodiments. Thus, A, B, and/or C can be replaced with A, B, and C written in one sentence and A, B, or C written in another sentence. A, B, and/or C means that some embodiments can include A and B, some embodiments can include A and C, some embodiments can include B and C, some embodiments can only include A, some embodiments can include only B, some embodiments can include only C, and some embodiments can include A, B, and C. The term "and/or" is used to avoid unnecessary redundancy.

The term "about" may be used to mean "approximately". For example, the disclosure includes "The inflation trough 68 may rotationally extend about 360 degrees around the perimeter 52 of the outer tube 20 in order to fluidly couple each inflation hole 66 of the plurality of inflation holes." In this context, "about 360 degrees" is used to mean "approximately 360 degrees". Any value between 270 and 360 degrees may fall within the range of "about 360 degrees" as used in the disclosure.

The term "substantially" may be used to mean "completely" or "nearly completely". For example, the disclosure includes "the plurality of inflation holes are substantially symmetrically spaced around the outer tube." In this context, "substantially symmetrically" means that the inflation holes are completely or nearly completely symmetrically spaced around the outer tube.

While certain example embodiments have been described, these embodiments have been presented by way of example only, and are not intended to limit the scope of the inventions disclosed herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions, and changes in the form of the methods and systems described herein may be made without departing from the spirit of the inventions disclosed herein.

What is claimed is:

1. A balloon guiding sheath, comprising:
an elongated sheath comprising a proximal end, a distal end, an inner tube extending between the proximal end and the distal end, an outer tube surrounding the inner tube and extending between the proximal end and the distal end, an access port located adjacent the proximal end, a distal port located adjacent the distal end, and a working lumen extending through an interior portion of the elongated sheath between the access port and the distal port;
an inflatable balloon located on an outer surface of the elongated sheath adjacent the distal end, the inflatable balloon being fluidly coupled to an inflation lumen via a plurality of inflation holes, the inflation lumen extending between the inflatable balloon and an inflation port located adjacent the proximal end; and
a textured surface located along an outer portion of the outer tube and located between the inflatable balloon and the inflation lumen, wherein the textured surface defines a first area and an inflatable portion of the inflatable balloon defines a second area, and wherein the second area is greater than the first area,
wherein the elongated sheath is sized and configured to enable direct insertion of the elongated sheath into a patient's vasculature through an arteriotomy to position the inflatable balloon at a target site,
wherein the plurality of inflation holes are located closer to a distal portion of the inflatable balloon than to a proximal portion of the inflatable balloon,
wherein the textured surface is located closer to the distal portion of the inflatable balloon than to the proximal portion of the inflatable balloon,
wherein the plurality of inflation holes are longitudinally aligned with the textured surface,
wherein the textured surface and the plurality of inflation holes are arranged and configured to facilitate substantially radially symmetric inflation of the inflatable balloon, and
wherein the textured surface is arranged and configured to reduce at least one of a contact area or surface energy between the outer tube and the inflatable balloon when the inflatable balloon is deflated compared to a configuration of the balloon guiding sheath in which the balloon guiding sheath does not include the textured surface.

2. The balloon guiding sheath of claim 1, wherein the textured surface defines at least one raised surface and at least one lowered surface.

3. The balloon guiding sheath of claim 1, wherein the textured surface rotationally extends around at least a portion of a perimeter of the outer tube.

4. The balloon guiding sheath of claim 3, wherein the textured surface rotationally extends 360-degrees around the perimeter of the outer tube.

5. The balloon guiding sheath of claim 1, wherein the textured surface is entirely located between the inflatable balloon and the inflation lumen.

6. The balloon guiding sheath of claim 1, wherein the textured surface comprises a cross-hatched surface.

7. The balloon guiding sheath of claim 1, wherein the textured surface defines a cross-sectional profile defining a rectangular shape.

8. The balloon guiding sheath of claim 1, wherein the textured surface defines a cross-sectional profile defining a triangular shape.

9. The balloon guiding sheath of claim 1, wherein the textured surface is located adjacent the distal end of the elongated sheath.

10. The balloon guiding sheath of claim 1, wherein the elongated sheath defines a generally constant outer diameter from the proximal end to the distal end.

11. The balloon guiding sheath of claim 1, wherein the plurality of inflation holes are substantially symmetrically spaced around the outer tube.

12. A method comprising:
inserting a balloon guiding sheath directly into vasculature of a patient through an arteriotomy, the balloon guiding sheath comprising:
an elongated sheath comprising a proximal end, a distal end, an inner tube extending between the proximal end and the distal end, an outer tube surrounding the inner tube and extending between the proximal end and the distal end, an access port located adjacent the proximal end, a distal port located adjacent the distal end, and a working lumen extending through an interior portion of the elongated sheath between the access port and the distal port;
an inflatable balloon located on an outer surface of the elongated sheath adjacent the distal end, the inflatable balloon being fluidly coupled to an inflation lumen via a plurality of inflation holes, the inflation lumen extending between the inflatable balloon and an inflation port located adjacent the proximal end; and
a textured surface located along an outer portion of the outer tube and located between the inflatable balloon and the inflation lumen, wherein the textured surface defines a first area, and an inflatable portion of the inflatable balloon defines a second area, and wherein the second area is greater than the first area,
wherein the plurality of inflation holes are located closer to a distal portion of the inflatable balloon than to a proximal portion of the inflatable balloon,
wherein the textured surface is located closer to the distal portion of the inflatable balloon than to the proximal portion of the inflatable balloon, and
wherein the plurality of inflation holes are longitudinally aligned with the textured surface;
advancing the balloon guiding sheath through the vasculature of the patient and positioning the distal end at a target site; and
inflating the inflatable balloon, wherein the textured surface and the plurality of inflation holes are arranged and configured to facilitate substantially radially symmetric inflation of the inflatable balloon.

13. The method of claim 12, wherein the textured surface is arranged and configured to reduce surface contact between the inflatable balloon and the outer tube compared to a configuration of the balloon guiding sheath in which the balloon guiding sheath does not include the textured surface.

14. The method of claim 12, wherein the textured surface is arranged and configured to reduce surface energy between the inflatable balloon and the outer tube compared to a configuration of the balloon guiding sheath in which the balloon guiding sheath does not include the textured surface.

15. The method of claim 12, wherein inflating the inflatable balloon comprises flowing at least one of fluid or media over the textured surface.

16. A balloon guiding sheath, comprising:
an elongated sheath comprising a proximal end, a distal end, an inner tube extending between the proximal end and the distal end, an outer tube surrounding the inner tube and extending between the proximal end and the distal end, an access port located adjacent the proximal end, a distal port located adjacent the distal end, and a working lumen extending through an interior portion of the elongated sheath between the access port and the distal port;
an inflatable balloon located on an outer surface of the elongated sheath adjacent the distal end, the inflatable balloon being fluidly coupled to an inflation lumen via a plurality of inflation holes, the inflation lumen extending between the inflatable balloon and an inflation port located adjacent the proximal end; and
a textured surface located along an outer portion of the outer tube and located between the inflatable balloon and the inflation lumen, wherein the textured surface defines at least one raised surface and at least one lowered surface, and wherein the textured surface defines a first area and an inflatable portion of the inflatable balloon defines a second area greater than the first area,
wherein the elongated sheath is sized and configured to enable direct insertion of the elongated sheath into a patient's vasculature through an arteriotomy to position the inflatable balloon at a target site, and
wherein the plurality of inflation holes are located closer to a distal portion of the inflatable balloon than to a proximal portion of the inflatable balloon, wherein the plurality of inflation holes are longitudinally aligned with the textured surface, and wherein the textured surface and the plurality of inflation holes are arranged and configured to facilitate substantially radially symmetric inflation of the inflatable balloon.

17. The balloon guiding sheath of claim 16, wherein the textured surface rotationally extends around at least a portion of a perimeter of the outer tube.

18. The balloon guiding sheath of claim 16, wherein the textured surface is entirely located between the inflatable balloon and the inflation lumen.

* * * * *